(12) United States Patent
Gropp et al.

(10) Patent No.: US 8,389,762 B2
(45) Date of Patent: Mar. 5, 2013

(54) METHOD FOR PURIFYING METHACRYLIC ACID

(75) Inventors: Udo Gropp, Bad Endorf (DE); Stefanie Sohnemann, Overath (DE); Guido Protzmann, Bensheim (DE); Thomas Mertz, Bensheim (DE)

(73) Assignee: Evonik Röhm GmbH, Darmstadt (DE)

( * ) Notice: Subject to any disclaimer, the term of this patent is extended or adjusted under 35 U.S.C. 154(b) by 322 days.

(21) Appl. No.: 12/812,258

(22) PCT Filed: Jan. 13, 2009

(86) PCT No.: PCT/EP2009/050295
§ 371 (c)(1),
(2), (4) Date: Jul. 9, 2010

(87) PCT Pub. No.: WO2009/115350
PCT Pub. Date: Sep. 24, 2009

(65) Prior Publication Data
US 2010/0314239 A1   Dec. 16, 2010

(30) Foreign Application Priority Data
Mar. 20, 2008   (DE) .......................... 10 2008 000 787

(51) Int. Cl.
*C07C 57/065* (2006.01)
*C07C 57/07* (2006.01)

(52) U.S. Cl. ........................................ 562/600; 562/598
(58) Field of Classification Search ........................ None
See application file for complete search history.

(56) References Cited

U.S. PATENT DOCUMENTS

| 3,320,305 | A | 5/1967 | Wiese et al. |
| 3,515,750 | A | 6/1970 | Schroeder |
| 5,041,646 | A | 8/1991 | Gebauer |
| 7,253,307 | B1 * | 8/2007 | Carlson et al. ................ 562/526 |
| 2009/0299023 | A1 | 12/2009 | Gropp et al. |
| 2010/0029881 | A1 | 2/2010 | Gropp et al. |
| 2010/0056742 | A1 | 3/2010 | Gropp et al. |
| 2010/0069594 | A1 | 3/2010 | Gropp et al. |
| 2010/0069662 | A1 | 3/2010 | Gropp et al. |
| 2010/0076214 | A1 | 3/2010 | Gropp et al. |

FOREIGN PATENT DOCUMENTS
GB          1 100 370          1/1968

* cited by examiner

*Primary Examiner* — Yevegeny Valenrod
(74) *Attorney, Agent, or Firm* — Oblon, Spivak, McClelland, Maier & Neustadt, L.L.P.

(57) ABSTRACT

The present invention relates to a process for purifying methacrylic acid, wherein the reaction mixture obtained by a reaction of methacrylamide with water is cooled by mixing with an aqueous medium and then passed into a phase separator. The present invention further describes a system for performing the process according to the invention.

20 Claims, 4 Drawing Sheets

METHOD FOR PURIFYING METHACRYLIC ACID

The present invention relates to a process for purifying methacrylic acid and to a system for performing this process.

Processes for preparing methacrylic acid have been known for some time. A customary procedure consists in the controlled oxidation of hydrocarbon gases, for example propylene or butylene. Disadvantages of this process are the yields obtained thereby, which are rather low when viewed overall.

In addition, methacrylic acid can be obtained by the reaction of methacrylamide with water. This process is described especially in U.S. Pat. No. 7,253,307. According to this publication, the reaction of the methacrylamide with water can be effected in a stirred tank reactor or a tubular reactor. Preference is given to performing the reaction at a pressure in the range of 3.65 to 7.70 bar and a temperature in the range of 50 to 210° C. The resulting reaction mixture is cooled by a heat exchanger and passed into a phase separator. Here, an aqueous phase is separated from an organic phase. The desired product is then isolated from the organic phase.

The processes described in U.S. Pat. No. 7,253,307 for preparing methacrylic acid already lead to good yields coupled with a high purity. However, methacrylic acid is an important product in the chemical industry which serves as a starting material for many important products. Therefore, a maximum yield, a particularly high purity coupled with low preparation costs, is essential for the economic success of a preparation process for such an important product. Even relatively small improvements with regard to the yields, the service lifes of the systems or similar process features lead to a significant advance with regard to the waste volumes and the preparation costs.

In view of the prior art, it is thus an object of the present invention to provide a process for preparing or for purifying methacrylic acid which can be performed in a particularly simple and inexpensive manner. In this process, especially the yield, the purity and the service life of the system for preparing methacrylic acid are to be increased. In addition, formation of undesired by-products is to be minimized. It was therefore a further object of the present invention to provide a system for preparing methacrylic acid which enables very inexpensive production of methacrylic acid.

These objects, and further objects which are not stated explicitly but which are immediately evident or discernable from the connections discussed herein by way of introduction, are achieved by a process having all features of Claim 1. Appropriate modifications to the process according to the invention are protected in subclaims. With regard to the system for performing the process, Claim 21 offers a solution to the problem of interest.

The present invention accordingly provides a process for purifying methacrylic acid, which is characterized in that the reaction mixture obtained by a reaction of methacrylamide with water, is cooled by mixing with an aqueous medium and then passed into a phase separator.

As a result of these measures, it is surprisingly possible to provide a process for preparing or for purifying methacrylic acid which has a particularly outstanding profile of properties. It is surprisingly possible through the process according to the invention to prepare methacrylic acid in a particularly simple, safe and inexpensive manner. In the process, it is possible, inter alia, to increase the yield, the purity and the service life of the system for preparing methacrylic acid. Furthermore, the formation of undesired by-products can be minimized by the process of the present invention. Preferred systems for performing the process of the present invention can make a contribution to the advantages mentioned in a not immediately foreseeable manner.

According to the present process, methacrylic acid is obtained by reaction of methacrylamide with water. This reaction can be referred to as hydrolysis or saponification.

The reaction can be effected batchwise or continuously, for example in a tubular reactor or a stirred tank reactor. In a particular aspect of the present invention, the reaction can be effected continuously in a tubular reactor. The terms "continuous" and "tubular reactor" are known in the technical field. Continuous reactions are understood especially to mean reactions in which reactants are added and products are removed from the reaction mixture over a prolonged period. Tubular reactors comprise at least one tubular region in which the reaction can proceed. These reactors typically have a relatively simple construction, and so the capital costs are comparatively low.

Within the tubular reactor, a pressure difference may preferably be present in flow direction of the reaction mixture. This pressure difference can, inter alia, be achieved through different subregions within the tubular reactor which are delimited from one another, for example by valves. In a preferred embodiment of the present invention, this feature can be generated by hydrostatic pressure, in which case the reaction mixture passes through a height difference in flow direction.

The pressure difference which is preferably present between the inlet of the reactants and the outlet of the products from the tubular reactor is not critical per se, though surprising advantages are exhibited clearly in the case of a high pressure difference. However, a high pressure difference is in many cases associated with high capital costs. Unexpected advantages can be achieved especially if the pressure difference is at least 0.5 bar, more preferably at least 1 bar and most preferably at least 1.5 bar. The pressure gradient here may assume any form, for example a stepped form. However, particular preference is given to processes in which the pressure is altered continuously. This can be brought about especially by means of tubular reactors whose axis, which is defined by the flow direction of the reaction mixture, is inclined with respect to the earth's surface. The angle of inclination is preferably about 90°, i.e. the tubular reactor is aligned essentially vertically in relation to the earth's surface, though relatively small deviations, for example of less than 10°, preferably less than 5°, can in many cases be tolerated.

In a particularly appropriate configuration, the reactants can be converted at a high pressure at the start of the reaction and at a lower pressure at the end of the reaction. This modification can preferably be configured by virtue of flow through a tubular reactor, which is inclined with respect to the earth's surface, from the bottom upward, such that the flow direction has a direction component which is aligned at right angles to the earth's surface.

The reaction can be effected at elevated or reduced pressure. Surprising advantages with regard to the yield and the purity of the product, and also the service lifes of the system, can be achieved especially by effecting the reaction at a pressure in the range of 1 bar to 8 bar, preferably 1.5 bar to 6 bar and more preferably in the range of 2 to 5 bar.

Appropriately, the conversion can be performed at the start of the reaction at a pressure in the range of 1.5 to 6 bar, especially 2 to 4.5 bar and more preferably 2.5 to 3.5 bar, and at the end of the reaction at a pressure in the range of 1 to 5 bar, more preferably 1.5 to 4 and most preferably 2 to 3 bar.

The reaction temperature may likewise be within a wide range. Advantages which are not foreseeable per se can, however, for example in relation to the yield, the reaction rate and the service life of the plant, be achieved by virtue of the reaction being performed at a temperature in the range of 90° C. to 150° C., preferably 100° C. to 140° C.

The improvements detailed above can surprisingly additionally be enhanced by converting the reactants at the start of the reaction at a lower temperature than at the end of the reaction. Appropriately, the temperature at the end of the reaction may be at least 5° C. higher, preferably at least 10° C. higher, than at the start of the reaction. The temperature at the end of the reaction is preferably at most 25° C. higher, preferably at most 20° C. higher, than at the start of the reaction. For example, the conversion at the start of the reaction may be at a temperature in the range of 100° C. to 130° C., preferably in the range of 105° C. to 125° C. and most preferably in the range of 110° C. to 120° C. Towards the end of the reaction, temperatures in the range of 110° C. to 150° C. are particularly preferred. In a particular configuration, the maximum temperature achieved may be at most 160° C., more preferably at most 150° C. and most preferably at most 135° C. Appropriately, the temperature can be measured and controlled at least two regions of the reactor.

As well as the reactants, the reaction mixture may comprise additives which are known in the technical field. These include especially catalysts, for example acids, and stabilizers which prevent polymerization of the unsaturated compounds.

The reaction can preferably be catalysed with acid, in which case sulphuric acid can be used with particular preference. The sulphuric acid can additionally be added to the reaction mixture. In addition, the sulphuric acid may already be present in one of the reactants, for example in the methacrylamide and/or water. The pH of the mixture used may preferably be in the range of 1 to 7, more preferably in the range of 1 to 2.

In order to prevent undesired polymerization of the unsaturated compounds, it is possible to use polymerization inhibitors in the reaction. These compounds, for example hydroquinones, hydroquinone ethers, such as hydroquinone monomethyl ether or di-tert-butylpyrocatechol, phenothiazine, N,N'-(diphenyl)-p-phenylenediamine, 4-hydroxy-2,2,6,6-tetramethylpiperidine 1-oxyl, p-phenylenediamine, methylene blue or sterically hindered phenols, are widely known in the technical field. These compounds can be used individually or in the form of mixtures and are generally commercially available. Reaction of the stabilizers usually consists in them acting as free-radical scavengers for the free radicals which occur in the course of polymerization. For further details, reference is made to the common technical literature, especially to Römpp-Lexikon Chemie; editors: J. Falbe, M. Regitz; Stuttgart, N.Y.; 10th Edition (1996); under "antioxidants", and the references cited there.

In principle, the tubular reactor can be charged with water by supplying water to the reactor from any desired source provided that this water has no ingredients that might adversely affect the hydrolysis reaction or the subsequent process stages. For example, demineralized water or spring water can be supplied to the reactor. However, it is likewise possible to supply a mixture of water and organic compounds to the reactor, as obtained, for example, in the purification of methacrylic acid. In a preferred embodiment of the process presented here, the reactor is charged at least partly with a mixture of water and such organic compounds. The molar ratio of water to methacrylamide in the reaction mixture used may, for example, be in the range of 7:1 to 1:1, more preferably 5.5:1 to 4:1.

Preferably, a mixture can be used which comprises 10 to 40% by weight, more preferably 20 to 30% by weight, of methacrylamide, 20 to 50% by weight, more preferably 26 to 32% by weight, of water, 30 to 65% by weight, more preferably 40 to 52% by weight, of sulphuric acid and 0 to 5% by weight, more preferably 0.1 to 4% by weight, of additional additives.

Surprising advantages can be achieved specially in the case of a residence time in the range of 10 minutes to 2 hours, more preferably 20 minutes to 1 hour.

For the success of the invention, it is essential that the reaction mixture obtained by the reaction is cooled by mixing with an aqueous medium and then passed into a phase separator. It is thus surprisingly possible to increase the service life of the system, while further advantages are also achieved. More particularly, this configuration allows the yield of methacrylic acid to be increased and the formation of by-products, especially solid constituents, in the reaction mixture to be minimized.

The aqueous medium by which the resulting reaction mixture is cooled preferably has a temperature in the range of 20° C. to 80° C., more preferably 40 to 75° C. The volume ratio of the reaction mixture obtained by the reaction relatively to aqueous medium may be in the range of 2:1 to 1:5, more preferably 1:1 to 1:3.

The aqueous medium to be used for cooling can be supplied fresh to the production process. The aqueous medium may, for example, consist of water or comprise further constituents which, however, should not exert an adverse effect on the reaction mixture. It is particularly appropriate to use an aqueous medium which is obtained by separation of the reaction mixture obtained by the reaction. This measure allows the costs to be lowered considerably. In a technically particularly favourable manner, the aqueous medium can be discharged from the phase separator. This configuration is possible as a result of the surprising finding that the aqueous phase obtainable in a separation in many cases comprises relatively low proportions of organic constituents, especially of solid by-products, and these proportions can be minimized further by purification or by means of a suitable volume of a first phase separator and the associated reflux ratio.

For the performance of the process according to the invention, a system may have exactly one phase separator in which the resulting reaction mixture is separated into an organic phase and an aqueous phase. A system preferably has two or more phase separators, such that the reaction mixture is introduced from a first phase separator into a second phase separator.

This configuration of the process allows the cooling circuit to be decoupled in a particularly simple and hence low-maintenance manner from the discharge of the inorganic phase. Among other reasons, the discharge of the inorganic phase present in the second phase separator can be controlled in order to achieve further improvements in the service life of the system. The control of the discharge of the inorganic phase can be effected by means of a pressure differential measurement and/or a capacitive measurement.

The discharge stream can be passed through a screen, such that relatively coarse particles are retained. The initially retained relatively coarse particles can preferably be mechanically comminuted. This comminution can be effected, for example, by means of turbulent flows. This configuration contributes to a further improvement in trouble-free operation of the system, this embodiment being enabled especially by the specific cooling of the reaction mixture, since this allows the by-product formation to be minimized to such a significant degree that only small amounts of relatively coarse particles have to be comminuted.

Organic compounds which are present in the aqueous phase removed can be isolated in a special modification of the process according to the invention. For this purpose, the aqueous phase removed can first be introduced into a tank charged with steam in order to drive out the organic constituents still present in the aqueous phase. The organic constituents driven out, which have a high proportion of methacrylic acid, can be purified and recovered.

In a particular configuration, the organic phase of the separated reaction mixture can be purified by a two-stage distillation. Preference is given to first removing low-boiling byproducts from the organic phase, such that crude methacrylic acid can be transferred from the bottom of the first still into a second still.

To remove low-boiling constituents of the organic phase, the crude methacrylic acid is preferably fed into the upper half of a distillation column. The column bottom is preferably heated so as to achieve a wall temperature of about 50 to about 120° C. The purification is typically effected under reduced pressure. The pressure within the column is preferably about 40 to about 300 mbar.

At the top of the column, the low-boiling constituents are removed. In particular, these may, for example, be ethers, acetone and methyl formate. The vapours are subsequently condensed by means of one or more heat exchangers. It has been found to be useful in some cases, for example, first to perform a condensation by means of two series-connected, water-cooled heat exchangers. However, it is equally possible also to use only one heat exchanger at this point. The heat exchangers are preferably operated in a vertical state to increase the flow rate and to achieve full surface wetting. Connected downstream of the water-cooled heat exchanger or the water-cooled heat exchangers may be a brine-cooled heat exchanger, but it is also possible to connect downstream a cascade of two or more brine-cooled heat exchangers. In a further configuration of the apparatus, low-boiling constituents can also be discharged via a low boiler outlet. In the cascade of heat exchangers, the vapours are condensed, provided with stabilizer and, for example, sent to a phase separator. Since the vapours may also comprise water, any aqueous phase obtained is disposed of or sent to a further utilization. One example of a possible further utilization is that of recycling into a hydrolysis reaction.

The organic phase removed may be fed partly as reflux into the top of the column. A portion of the organic phase can in turn be used to spray the heat exchanger tops and the column top. Since the organic phase removed is a phase admixed with stabilizer, it is thus possible to effectively prevent first the formation of calming zones. Secondly, the presence of the stabilizer brings about a further suppression of the polymerization tendency of the vapours removed.

The condensate stream obtained from the heat exchangers is additionally preferably admixed with demineralized water in such a way that a sufficient separating action can be achieved in the phase separator.

The gaseous compounds which remain after the condensation in the heat exchanger cascade may, preferably by means of steam ejectors as reduced pressure generators, once again be subjected to a condensation by means of one or more further heat exchangers. It has been found to be advantageous for economic reasons when such a postcondensation condenses not only the gaseous substances from the prepurification. For example, it is possible to feed further gaseous substances, as arise from the main purification of methacrylic acid, to such a postcondensation. The advantage of such a procedure lies, for example, in thus being able to transfer a proportion of methacrylic acid which has not been condensed in the main purification stage once more via the phase separator into the purification column for the purposes of prepurification. It is thus ensured, for example, that a maximization of yield can take place, and minimum losses of methacrylic acid occur. Moreover, the suitable selection of the design and of the operation of these further heat exchangers allows the composition of the offgas leaving these heat exchangers, especially the content of low boilers, to be adjusted.

For fine purification of the methacrylic acid, the crude, prepurified methacrylic acid is subjected to another distillation. This frees the crude methacrylic acid from the high-boiling constituents with the aid of a distillation column to obtain glacial methacrylic acid.

The distillation column can in principle correspond to any design which appears suitable to those skilled in the art. However, it has been found to be advantageous in many cases for the purity of the resulting product when the distillation column is operated with one or more packings which correspond approximately to the following requirements:

Firstly, just like in the other lines through which methacrylic acid flows, a minimum level of so-called "dead spaces" should form in the columns. The dead spaces lead to a comparatively long residence time of the methacrylic acid, which promotes its polymerization. Moreover, it has been found that, surprisingly, dead spaces are in many cases not serviced to a sufficient degree by optionally used stabilizers or stabilizer mixtures. The polymerization of methacrylic acid leads in turn to expensive production shutdowns and cleaning of the appropriate parts blocked with polymer. One way of countering the formation of dead spaces is, both through the design and through a suitable operating mode of the columns, to always load them with a sufficient amount of liquid, such that constant flushing of the columns and especially of the column internals such as packings is achieved. For instance, the columns may have spray devices which are designed for the spraying of the column internals. In addition, the column internals may be connected to one another such that no dead spaces arise. This is achieved by means of outlet orifices or interrupted adhesion seams, as described hereinafter. Such adhesion seams have at least 2, preferably at least 5 and more preferably at least 10 interruptions per 1 m of adhesion seam length. The length of these interruptions may be selected such that they make up at least about 10%, preferably at least about 20% and more preferably at least about 50%, but generally not more than 95%, of the adhesion seam length. Another design measure may be that, in the internal regions of the column, especially those which come into contact with the methacrylic acid, less than about 50%, preferably less than about 25% and more preferably less than about 10% of all surfaces, especially of column internals, run horizontally. For example, the stubs which open into the interior of the column may be configured conically or with oblique surfaces. Another measure may consist in keeping the amount of liquid methacrylic acid present in the column bottom as low as possible during the operation of the column, and another in preventing overheating of this amount in spite of moderate temperatures and large evaporation areas during the evaporation. It may be advantageous in this context that the amount of liquid in the column bottom amounts to in the range of about 0.1 to 15% and preferably about 1 to 10% of the total amount of methacrylic acid in the column.

In the purification of the methacrylic acid, high-boiling constituents thereof are separated from the product by distillation. The bottom temperature is preferably about 50 to about 80° C., especially about 60 to about 75° C., at a wall temperature of less than about 120° C.

The material obtained in the column bottom is preferably removed continuously and cooled by means of a heat exchanger or a cascade of a plurality of heat exchangers to a temperature in a range of about 40 to about 80° C., preferably about 40 to about 60° C. and more preferably in a range of about 50 to 60° C.

To improve the yield, the bottoms of the second still can once again be evaporated. These bottoms of the second still can preferably be evaporated with a circulation evaporator and introduced into the second still. This configuration is preferred over a thin-film evaporator for reasons of cost. However, circulation evaporators are more maintenance-intensive if solid by-products are present in the mixture to the evaporated. Surprisingly, however, surprisingly effectively cooling of the reaction mixture, which leads to unexpectedly low by-product formation and effective minimization of the solid constituents, makes it possible to use circulation evaporators.

At the top of the column, the methacrylic acid purified by distillation is withdrawn and cooled by means of a heat exchanger or a cascade of two or more heat exchangers. In this case, the heat of the vapours can be removed by water-cooled heat exchangers or by brine-cooled heat exchangers or by a combination of the two. It has been found to be useful in some cases when the vapours from the distillation column are transferred into two or more heat exchangers connected in parallel, which are operated by means of water cooling. The uncondensed fractions from the water-cooled heat exchangers can, for example, be introduced into a brine-cooled heat exchanger or a cascade of two or more brine-cooled heat exchangers which may be arranged in series or in parallel. In a further configuration of the apparatus, low-boiling constituents can also be removed via a low-boiler outlet. The condensates obtainable from the heat exchangers are introduced into a collecting vessel and sent to a buffer vessel by means of a pump via a further heat exchanger or a cascade of two or more further heat exchangers. The condensate stream is cooled, for example, by means of a cascade of one or two water-cooled heat exchangers and one or two brine-cooled heat exchangers to a temperature in a range of about 18 to about 50° C., preferably about 18 to about 40° C. and more preferably in a range of about 18 to 30° C.

A substream is withdrawn from the condensate stream and is recycled into the distillation column via the top of the column. The condensate stream can in principle be fed into the top of the column in any desired manner, for example via distributors. However, it may be advantageous when a portion of the condensate stream is fed into the vapour line above the top of the column, for example sprayed in. It is also preferred that this feeding introduces stabilizer into the top of the column.

A further substream of the condensate intended for recycling into the column can, for example, be branched off before introduction into the vapour line and be introduced directly into the top of the column. Here too, it is preferred that this introduction introduces stabilizer into the top of the column. The introduction into the top of the column can be done, for example, in such a way that the interior of the top of the column is sprayed with a condensate such that no calming zones can form in the top of the column, at which the methacrylic acid can polymerize. It may additionally be advantageous to add a stabilizer for preventing polymerization to a condensate substream which is recycled into the column. This can be done, for example, by adding an appropriate amount of polymerization inhibitor as a stabilizer to the condensate substream intended for spraying of the top of the column. It has been found to be advantageous in some cases when the condensate substream, after the addition of the stabilizer but before entry into the top of the column, passes through a suitable mixing apparatus, preferably a static mixer, in order to achieve very substantially uniform distribution of the stabilizer in the condensate substream.

The uncondensable gaseous substances which are obtained in the purification process are, for example, sent to disposal.

The system for performing the present process may comprise known reactors for reacting amides with water. These include especially stirred tank reactors and tubular reactors. Preference is given to using an essentially vertically aligned tubular reactor. This allows surprising advantages to be achieved with regard to the service lifes of the system, and to the yield and product purity.

The tubular reactor preferably has at least two, more preferably at least three, heat exchangers, by means of which the reaction temperature can be adjusted to a desired profile.

The reactants can be introduced into the tubular reactor via a pump. To avoid maintenance-related operation shutdowns, it is also possible to provide two or more pumps which can be connected in parallel. Viewed in flow direction, the reactants can appropriately be mixed upstream of the pumps, in which case the system more preferably has no further internals for mixing in the region between the pumps and the tubular reactor. These measures allow surprising advantages to be achieved with regard to operational reliability and the service lifes of the system, and in relation to the yield and the purity of the product.

A preferred system for performing the process according to the present invention has at least one phase separator, said phase separator being connected by a recycle line to the feed line through which the reaction mixture is passed into the phase separator. Such a system likewise forms part of the subject-matter of the present invention.

The recycle line through which the phase separator may preferably be connected to the feed line through which the reaction mixture may preferably be passed into the phase separator may preferably be equipped with a heat exchanger. This allows the temperature of the phase recycled to be controlled.

The system may have one, two or more phase separators, preference being given to systems with at least two phase separators. Appropriately, the first phase separator may be connected by a recycle line to the feed line through which the reaction mixture is passed into the phase separator. The second phase separator preferably comprises an apparatus for controlling the inorganic discharge. The second phase separator preferably has a greater volume than the first phase separator. The second phase separator may comprise at least one withdrawal point at which at least one screen which retains relatively coarse particles is provided. In this case, the withdrawal point is preferably modified such that the relatively coarse particles retained by the screen are mechanically comminuted. The mechanical comminution can in particular be brought about by a turbulent flow, in which case the friction on the particles achieved as a result at the screen leads to comminution. For example, the screen can be configured in the form of an inserted tube provided with bores.

The components of the system which come into contact with acid, especially the tubular reactor, the pumps and the phase separator, are preferably constructed from an acid-resistant metal, for example zirconium, tantalum, titanium or stainless steel, or a coated metal which has, for example, an enamel layer or a zirconium layer. In addition, it is also possible to use plastics, for example PTFE-sheathed components, graphitized components or materials composed of graphite, especially in pumps.

The methacrylamide used to prepare methacrylic acid can preferably be obtained by the so-called ACH process. Proceeding from hydrogen cyanide and acetone, acetone cyanohydrin is prepared in a first step and is then converted to methacrylamide. These steps are described, inter alia, in U.S. Pat. No. 7,253,307, EP-A-1 666 451 and DE 102006058251.9.

The above will now be illustrated by way of example with reference to nonlimiting drawings. The system described in the figures relates in the present context to a system for preparing methacrylic acid. The figures show.

Figure 1:
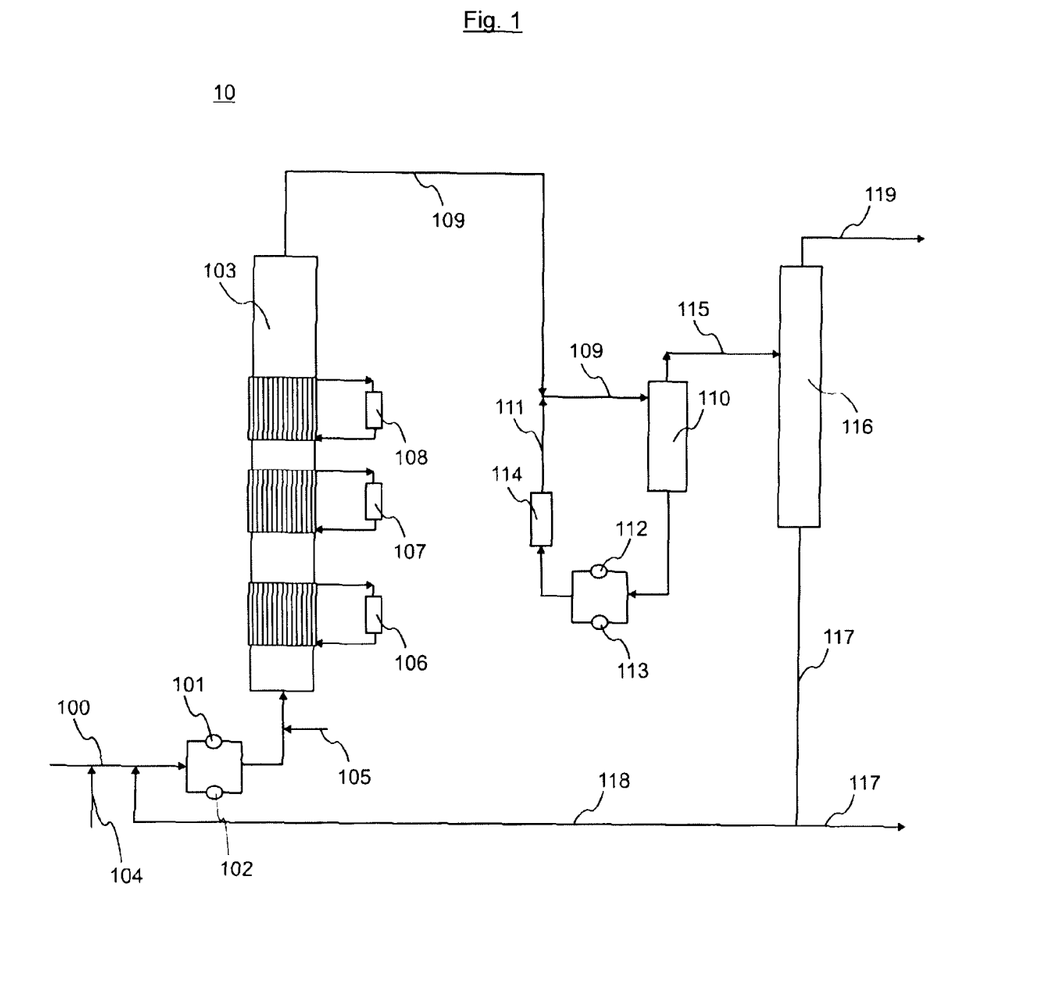
FIG. 1: a schematic of a system for reacting methacrylamide with water.

FIG. 1 shows a preferred embodiment of a system 10 in which the methacrylamide is reacted with water. Through lines 100, the amide, conveyed by pumps 101 and 102, is passed into the tubular reactor 103. The water required for the reaction can be fed via an external source into line 100, which is connected to line 100 via line 104 in FIG. 1. In addition, at least a portion of the water from a phase separator 116 which will be described later can be introduced via line 118 into line 100. In this case, the supply, viewed in flow direction, can be effected upstream of pumps 101 and 102. Pumps 101 and 102 are connected in parallel. A parallel connection of pumps 101 and 102 allows the operational reliability to be increased. To stabilize the reaction mixture, stabilizers can be added through line 105.

The temperature of the tubular reactor 103 can preferably be controlled by two, more preferably three, heat exchangers 106, 107 and 108 which, in the present case, are configured as an integral constituent of the tubular reactor. For this purpose, it is possible to use cooling fluids which are passed through jackets which are provided at various segments of the tubular reactor.

The converted reaction mixture is discharged via line 109, which leads into a first phase separator 110. In the first phase separator, a portion of the aqueous phase is removed. This portion of the aqueous phase is recycled via line 111 into line 109. This circuit is maintained by the pumps 112, 113 connected in parallel. To improve the cooling performance of the aqueous phase recycled via line 111, the embodiment shown in the present case has a heat exchanger 114.

The cooled reaction mixture is passed via line 115 from the first phase separator 110 into the second phase separator 116. The second phase separator 116 may especially have a device for controlling the discharge, which is not shown in the present figure. The aqueous phase is discharged via line 117, and a portion of the aqueous phase can be introduced into the amide-conducting line 100 especially through line 118.

The portion of the aqueous phase which is not recycled can be worked up. A system suitable for this purpose is shown schematically in FIG. 4. The organic phase is discharged from this part of the plant via line 119. The organic phase is preferably purified by means of a two-stage process. The system shown in FIG. 1 may have gas separators, which are not shown, at various points. Advantageously, a gas separator may be provided especially downstream of the second phase separator 116 and upstream of the distillation system.

Figure 2:
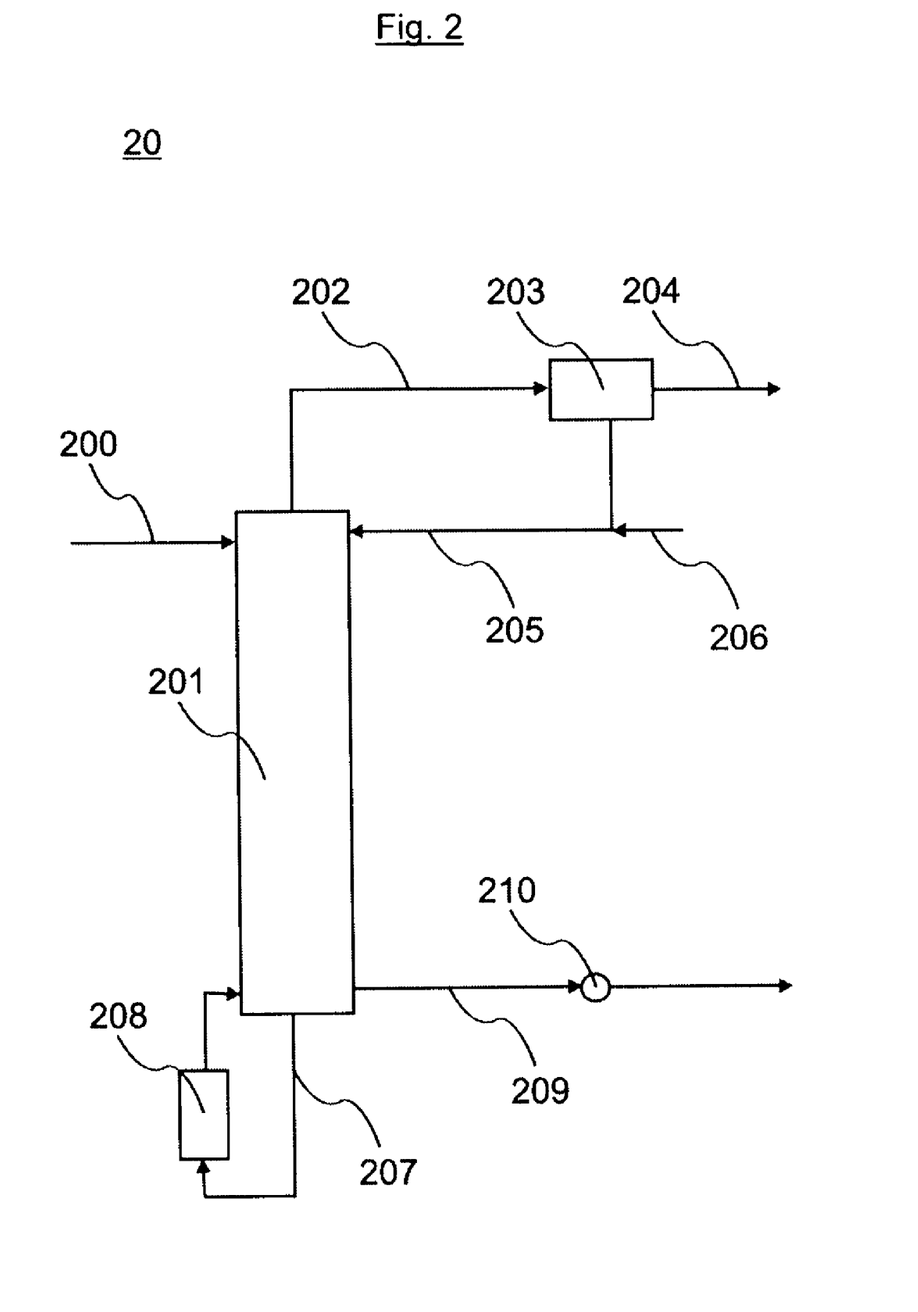
FIG. 2: a schematic of a system for prepurifying methacrylic acid.

FIG. 2 shows a preferred distillation system 20, by means of which the low-boiling constituents of the organic phase which can be obtained from the reaction mixture are removed.

An organic phase which can be obtained, for example, by a discharge from the system 10 shown in FIG. 1 is introduced via line 200 into the distillation column 201. The introduction can be effected, for example, in the region of the top of the column. The low-boiling constituents can be transferred from the top region of the distillation column 201 via line 202 into a heat exchanger 203. In the heat exchanger 203, the vapours are cooled and discharged via line 204, and a portion of the condensed substances can be recycled into column 201 through line 205. For stabilization, a stabilizer composition can be introduced into the column. This can be done, for example, via the feed 206, through which a stabilizer mixture can be introduced into line 205.

A portion of the column bottoms can be evaporated in a bottoms evaporator 208 via line 207 and be passed back into the column. The bottoms of the column can be discharged from the system by pump 210 via line 209.

Figure 3:
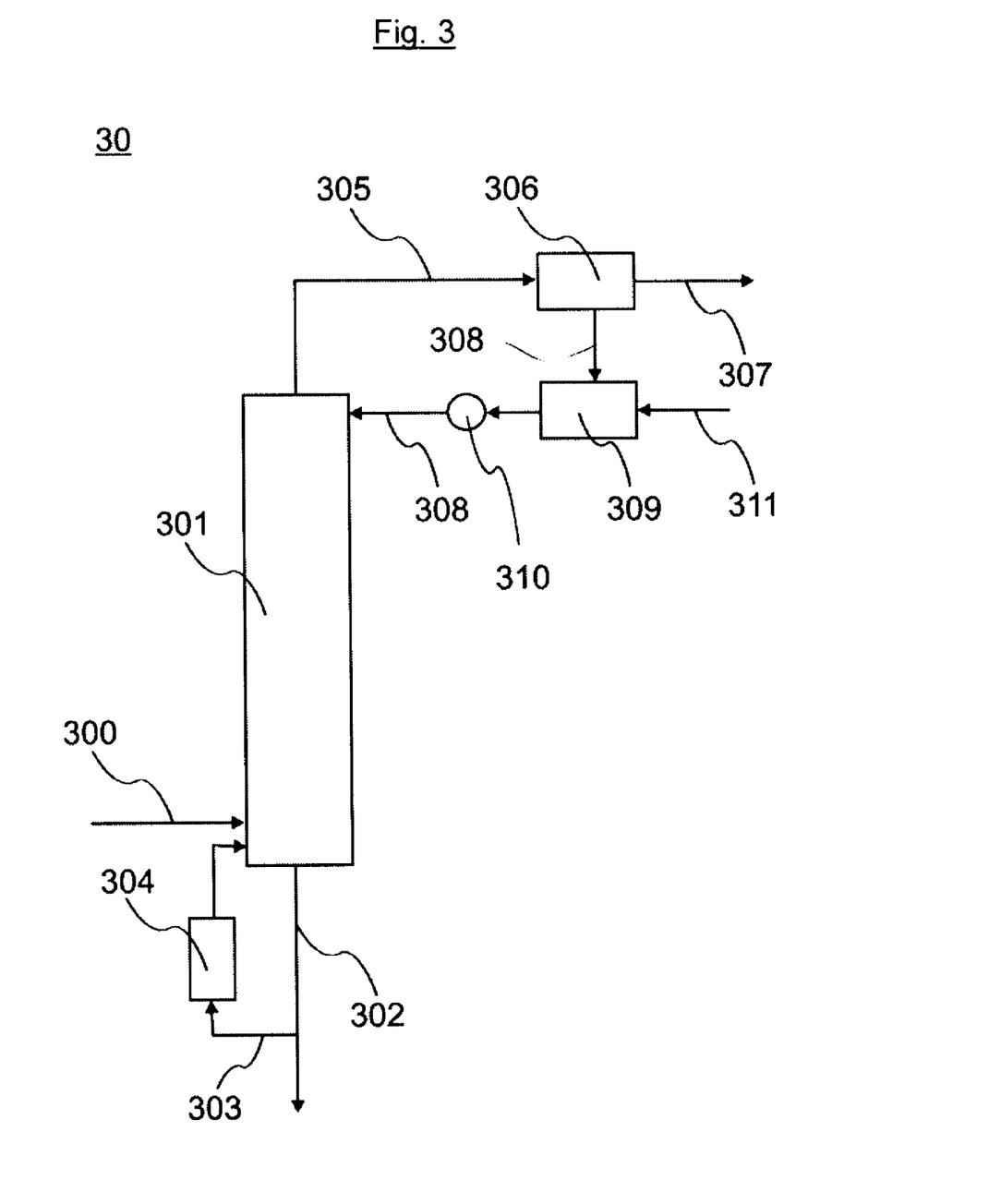
FIG. 3: a schematic of a fine purification system for methacrylic acid.

FIG. 3 shows a preferred embodiment of a distillation system 30, with which the methacrylic acid obtained in the bottoms of the above-described distillation system can be purified further.

A methacrylic acid-containing composition can be introduced via line 300 into the distillation column 301. High-boiling constituents of this composition are discharged from the column through the bottoms via line 302. A portion of this discharge can be evaporated in a bottoms evaporator 304, which is preferably configured as a circulation evaporator, through line 303 and be introduced into the bottom of column 301.

The methacrylic acid-containing vapours are withdrawn from the column via line 305 and condensed in the heat exchanger 306. The condensed methacrylic acid is withdrawn from the distillation system 30 through line 307. A portion of the phase condensed in the heat exchanger 306 can be introduced through line 308 into a second heat exchanger 309 and be cooled there. By means of the pump 310, the phase thus cooled can be introduced into the top of the distillation column 301. To stabilize the composition present in the distillation column 301, stabilizers can be used. Stabilizers can be fed in, for example, through line 311, through which stabilizers can be introduced into the heat exchanger 309.

Figure 4:
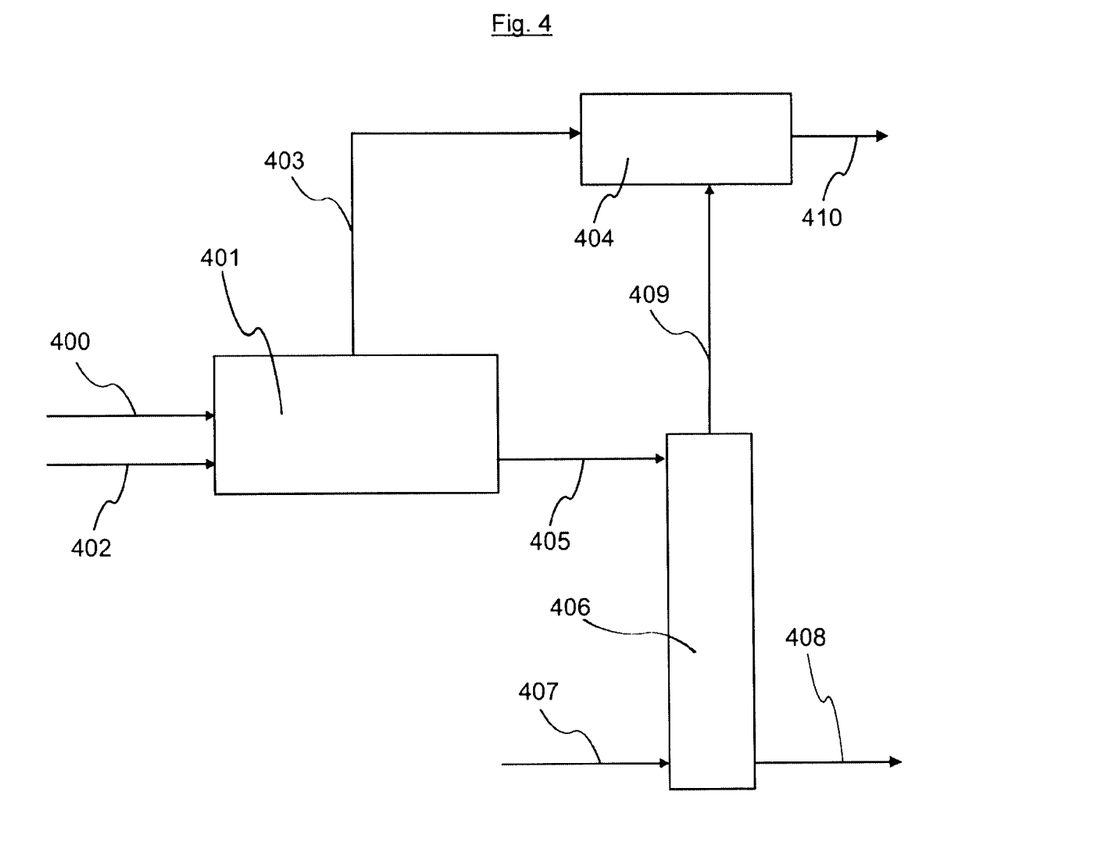
FIG. 4: a schematic of a system for stripping the aqueous phase which is obtained from the system for hydrolysing methacrylamide.

FIG. 4 shows a schematic of a preferred system for stripping the aqueous phase which is obtained from the system 10 for hydrolysing the methacrylamide. The aqueous phase can be introduced via line 400 into an acid vessel 401 which is charged with steam via feed 402. The gaseous substances released as a result are discharged via line 403 into a condenser 404. The aqueous phase is transferred via line 405 into a column 406, which is likewise charged with steam via a feed 407. The aqueous discharge can be discharged through line 408. The vapour phase is introduced via line 409 into a condenser 404. The condensed phase is withdrawn from the system via line 410 and can, inter alia, be sent to the hydrolysis process shown in FIG. 1, since this phase has a high proportion of water and volatile organic constituents, especially of methacrylic acid and methacrylamide.

The present invention will be illustrated hereinafter using an example, without the intention that this should impose a restriction.

Example 1

Methacrylic acid (MA) is prepared in a system shown in FIG. 1. In this system, with tubular reactor 103 (reactor;

H=19.7 m, D=0.78 m, max. perm. pressure: 6 bar, max. perm. temperature: 200° C.), virtually trouble-free operation of the system over more than 6 months is ensured. In the course of this, the system loading can be varied within wide ranges. Loads up to 20 000 tonnes of MA per year with a purity of at least 99.5% (HPLC) are achieved.

The invention claimed is:

1. A process for purifying methacrylic acid, wherein the reaction mixture obtained by a reaction of methacrylamide with water is cooled when mixing with an aqueous medium and then passed into a phase separator.

2. The process according to claim 1, wherein the aqueous medium is obtained by separating the reaction mixture obtained in the reaction.

3. The process according to claim 2, wherein the aqueous medium is discharged from the phase separator.

4. The process according to claim 1, wherein the aqueous medium has a temperature in a range of 20° C. to 80° C.

5. The process according to claim 1, wherein the reaction mixture is introduced from a first phase separator into a second phase separator.

6. The process according to claim 5, wherein discharge of the inorganic phase present in the second phase separator is controlled.

7. The process according to claim 6, wherein the discharge of the inorganic phase is controlled by a pressure differential measurement and/or a capacitive measurement.

8. The process according to claim 5, wherein a discharge stream is passed through a screen such that relatively coarse particles are retained.

9. The process according to claim 8, wherein the relatively coarse particles are mechanically comminuted.

10. The process according to claim 1, wherein a the volume ratio of the reaction mixture obtained in the reaction relative to aqueous medium is within a range of 2:1 to 1:5.

11. The process according to claim 1, wherein the reaction is effected at a temperature from 90° C. to 150° C.

12. The process according to claim 1, wherein the reaction is effected at a pressure of 1.5 bar to 6 bar.

13. The process according to claim 1, wherein the reaction is carried out in a tubular reactor flowing through from bottom upward.

14. The process according to claim 1, wherein the reaction is catalyzed with acid.

15. The process according to claim 1, wherein the reaction mixture comprises at least one stabilizer.

16. The process according to claim 1, wherein a mixture is employed comprising:
   10 to 40% by weight of methacrylamide;
   20 to 50% by weight of water;
   30 to 65% by weight of sulphuric acid; and
   0 to 5% by weight of additional additives.

17. The Process according to claim 1, wherein the pH of the reaction mixture employed is from 1 to 2.

18. The Process according to claim 1, wherein residence time is from 10 minutes to 2 hours.

19. The Process according to claim 1, wherein an organic phase separated from the reaction mixture is purified by a two-stage distillation, comprising a first still and a second still.

20. The Process according to claim 19, wherein a bottom portion of the second still is evaporated with a circulation evaporator and introduced into the second still.

* * * * *